United States Patent [19]
Griswold

[11] Patent Number: 5,957,918
[45] Date of Patent: Sep. 28, 1999

[54] FAIL-SAFE CRYOSURGICAL INSTRUMENT

[75] Inventor: Thomas A. Griswold, Ellington, Conn.

[73] Assignee: Brymill Corporation, Vernon, Conn.

[21] Appl. No.: 09/032,379

[22] Filed: Feb. 26, 1998

[51] Int. Cl.[6] .................................................. A61B 17/36
[52] U.S. Cl. ............................ 606/20; 62/45.1; 251/254
[58] Field of Search ........................ 606/20–27; 62/45.1, 62/50.1, 51.1, 50.7, 293; 220/254, 284, 288; 215/314, 329; 222/568; 251/254

[56] References Cited

U.S. PATENT DOCUMENTS

| | | |
|---|---|---|
| 947,382 | 1/1910 | Goosman . |
| 2,602,628 | 7/1952 | Turenne et al. . |
| 3,630,403 | 12/1971 | Berg . |
| 5,222,999 | 6/1993 | Byrne ........................................... 374/5 |
| 5,649,639 | 7/1997 | Dolvet et al. ........................... 220/257 |
| 5,775,541 | 7/1998 | Perkins .................................... 222/105 |

*Primary Examiner*—Linda C. M. Dvorak
*Assistant Examiner*—Roy Gibson
*Attorney, Agent, or Firm*—M. P. Williams

[57] ABSTRACT

In a cryosurgical instrument having a dewar and a cap which is threaded onto the dewar when in use, with a main valve portion secured to the cap by threads, the handedness of the threads on the main valve portion are opposite to the handedness of the cap threads, whereby applying thrust through the main valve portion to remove the cap from the dewar will tend to tighten, rather than loosen the main valve portion in the cap.

6 Claims, 2 Drawing Sheets

FAIL-SAFE CRYOSURGICAL INSTRUMENT

RELATED INVENTIONS

The subject matter herein relates to commonly owned, U.S. patent applications filed contemporaneously herewith entitled "Cryosurgical Instrument", Ser. No. 09/084,205 (Docket No. B-44) and entitled "Venting Cryosurgical Instrument", Ser. No. (Docket No. B-45).

TECHNICAL FIELD

This invention relates to a liquid nitrogen storage and delivery system having an evacuated dewar, a cap on said dewar and a main valve mounted on the cap, in which the threads holding the valve to the cap have an opposite handedness from the threads that hold the cap on the dewar, whereby pressure on the main valve utilized to loosen the cap from the dewar will tighten, rather than loosen, the main valve.

BACKGROUND ART

A cryosurgical instrument disclosed in U.S. Pat. No. 4,269,390 employing a standard, double walled, evacuated, metal vacuum bottle or dewar, has a collar metallurgically bonded to the top of the dewar near the mouth thereof to provide machine threads for releasably engaging a cap having internal threads which comprises the delivery and control portion of the instrument. The cap has a valve mounted thereon which controls the flow of nitrogen from a feed tube in the dewar to a nozzle mounted on a delivery tube. The valve is opened by a valve operating lever. The cryosurgical instrument of said patent has been in service around the world, with minor modifications, since 1976. Sometimes, the main valve becomes loose and leakage results.

DISCLOSURE OF INVENTION

Objects of the invention include eliminating loosening of the main valve and related leaks in a cryosurgical instrument.

This invention is predicated on the discovery that when the unit is first filled and the cap is screwed onto the dewar, it can be made sufficiently tight rather easily, simply by gripping diametrically opposite portions of the cap (just as one would return the cap onto a food jar); however, after the instrument has been in use and has cooled down, it takes additional force to initially loosen the cap; this additional force, it has been found, is usually provided by grasping the delivery tube and/or the valve operating lever in order to provide a more secure grip on the cap. Heretofore, the threads securing the main valve to the cap have been of the same handedness as the threads on the cap itself, so that counterclockwise rotation of the main valve by applying pressure to the delivery tube and/or the valve operating lever also has a tendency to loosen the valve within the cap, thereby causing leakage.

According to the present invention, threads which secure the main valve portion of a cryosurgical instrument to a cap, which in turn is threaded onto the dewar portion, have threads which are of opposite handedness from the threads with which the cap is secured to the dewar. In a preferred embodiment of the invention, in order to be in accord with human expectation, the cap and dewar have right hand threads, and the main valve is secured to the cap utilizing lefthand threads. In a preferred embodiment of the invention, the valve passes through a clearance hole in the cap and is secured to the cap by means of a nut. In another embodiment, the cap may be threaded so as to receive the valve.

The invention overcomes the tendency to loosen the main valve of a cryosurgical instrument as a consequence of applying pressure to components attached to the valve when removing the cap of the instrument from the dewar thereof.

Other objects, features and advantages of the present invention will become more apparent in the light of the following detailed description of exemplary embodiments thereof, as illustrated in the accompanying drawing.

BEST MODE FOR CARRYING OUT THE INVENTION

Figure 1:
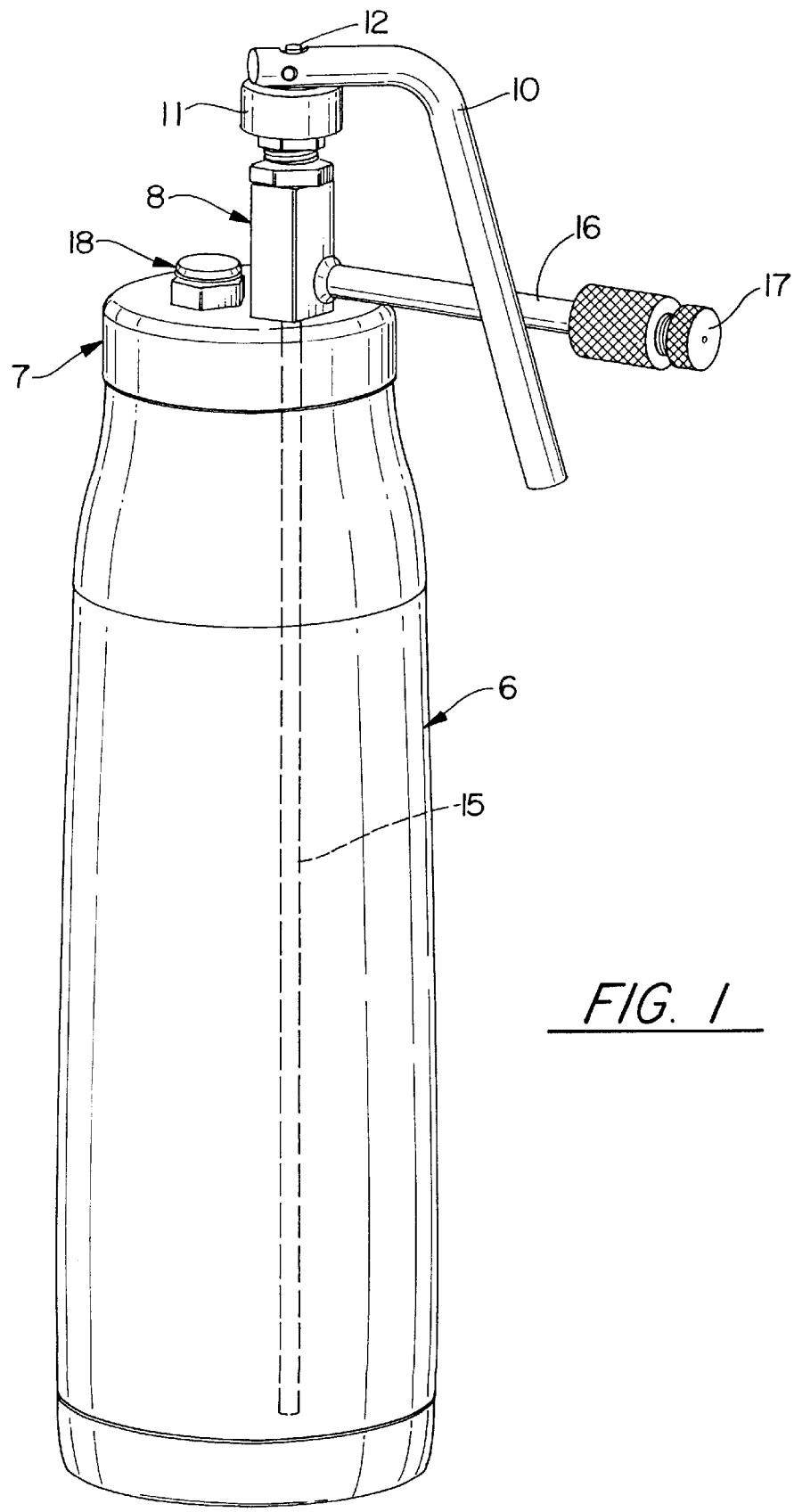
FIG. 1 is a perspective view of a cryosurgical instrument in which the present invention may be practiced.

Referring to FIG. 1, a cryosurgical instrument in which the present invention may be practiced includes a dewar 6, at the opening of which are threads to receive a threaded cap 7 which comprises the delivery and control portion of the instrument. The cap 7 has a main valve 8 disposed thereon, the valve having a valve operating lever 10 working with a fulcrum 11 to raise a stem 12 of a valve so as to regulate the flow of cryogenic fluid from within the dewar 6 along a feed tube 15 into a delivery tube 16 to a nozzle 17. The fluid pressure within the dewar 6 is maintained by a pressure relief valve 18. The functions, although not the appearance, of the instrument as thus far described are similar to those in said patent.

After the device has been in use for some time, it may be desirable to open it, either to add more cryogenic liquid to the dewar 6, or to remove the remaining cryogenic liquid from the dewar 6, for safety purposes. Typically, the unit is then cold, meaning that it is uncomfortable to grasp firmly for any length of time, and the cap may not be able to be turned with the same force that was used to tighten the cap when the cap is first installed on the dewar 6. In such a case, a natural tendency is to press against the valve operating lever 10 and the delivery tube 16 so as to provide extra torque, thereby assisting the operator in loosening the cap 7. In such a case, assuming right hand threads, counterclockwise rotation of the main valve 8 may cause it to be loosened with respect to the cap 7.

Figure 2:
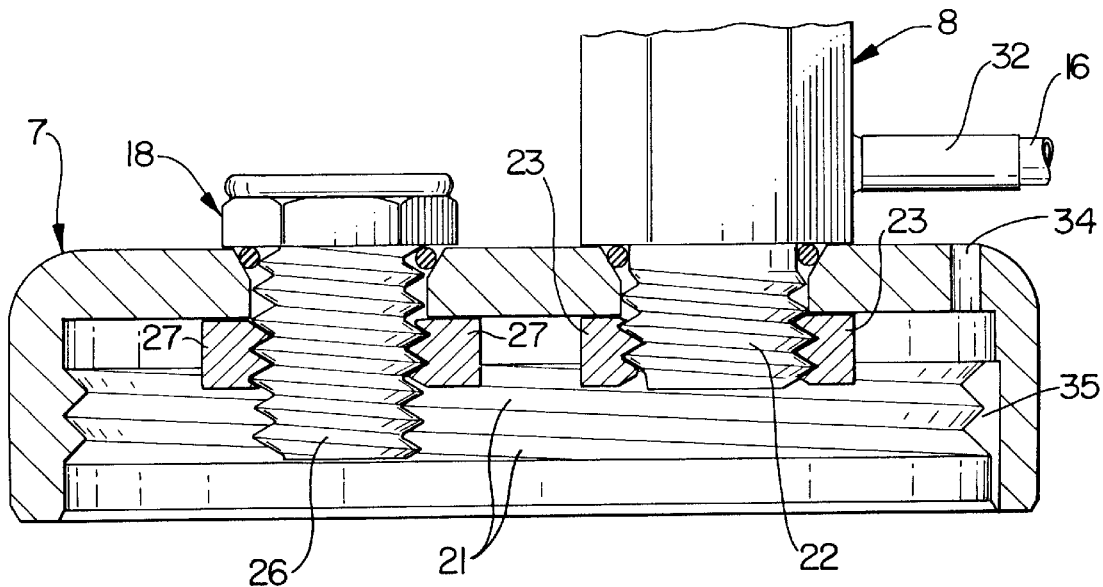
FIG. 2 is a partial, sectioned side elevation view of the cap of the cryosurgical instrument of FIG. 1 in a preferred embodiment which utilizes a nut to secure the main valve to the cap.

Referring to FIG. 2, the cap 7 is shown having right hand threads 21 such that turning of the cap 7 clockwise will cause the cap to be secured to the dewar 6, while turning the cap 7 counterclockwise will release the cap 7 from the dewar 6. In accordance with the invention, the main valve 8 has lefthand threads 22 on a portion thereof, and is secured to the cap 7 by means of a lefthand threaded nut 23. In the preferred embodiment, the pressure release valve 18 will similarly be provided with lefthand threads 26 and secured to the cap 7 by means of a lefthand threaded nut 27, so that the manufacturing operations of securing the nuts 23, 27 will be in the same direction, making it more facile for the assembler.

Instead of using nuts 23, 27, if desired, a cap 7a may be provided with threads 29, 30 (FIG. 3) so that the main valve 8 and pressure relief valve 18 will be screwed directly into the cap. However, the use of a nut 23 for the main valve 8 is preferred since it allows positioning the feed tube 16 is aligned with a radius of the cap.

Figure 3:
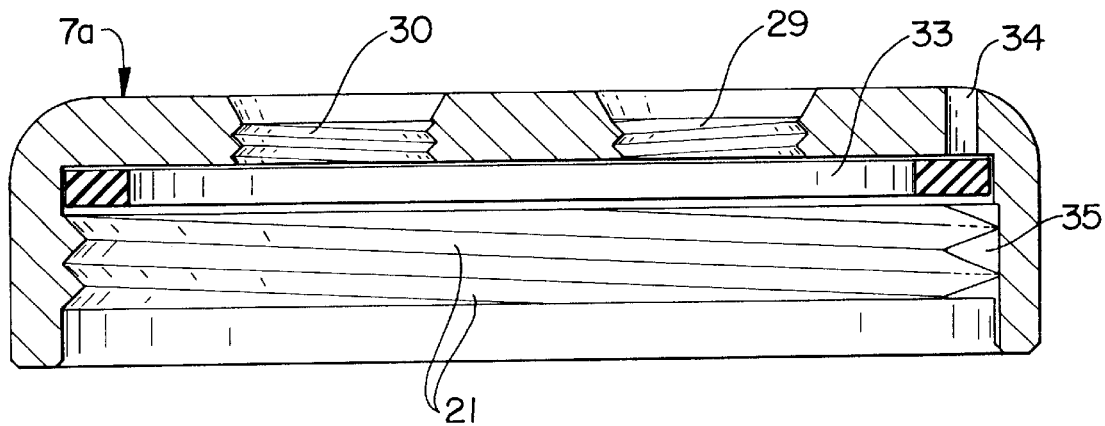
FIG. 3 is a sectioned, side elevation view of a cap of the cryosurgical instrument of FIG. 1 in an embodiment having threads to receive the main valve in accordance with the invention.

FIG. 3 also illustrates that the invention can be practiced if the threads of the pressure relief valve 18 are not of the same handedness as the threads of the main valve 8. FIGS. 2 and 3 also illustrate a gas relief hole 34 and a scalloped region 35, in which a small area of the threads 21 are machined away so as to provide a gas passage, all as is described and claimed in the aforementioned copending application Serial No. (Attorney Docket No. B-45).

Thus, although the invention has been shown and described with respect to exemplary embodiments thereof, it should be understood by those skilled in the art that the foregoing and various other changes, omissions and additions may be made therein and thereto, without departing from the spirit and scope of the invention.

I claim:

1. A cryosurgical instrument comprising:

a dewar having first threads at the mouth thereof;

a cap having second threads complementary to the threads of said dewar; and a main valve portion secured by means of third threads to said cap;

wherein the improvement comprises:

the handedness of said third threads of said main valve portion being opposite to the handedness of said second threads of said cap, whereby torque applied to said main valve portion to assist in loosening said cap from said dewar will tend to tighten said main valve portion in said cap.

2. A cryosurgical instrument according to claim 1 wherein said main valve portion is secured to said cap by means of a nut having fourth threads which are complementary to said third threads on said main valve portion.

3. A cryosurgical instrument according to claim 1 further comprising:

a pressure relief valve secured to said cap portion by means of fifth threads.

4. A cryosurgical instrument according to claim 3 wherein the handedness of said fifth threads of said pressure relief valve is the same as the handedness of said third threads of said main valve.

5. A cryosurgical instrument according to claim 3 wherein the handedness of said fifth threads of said pressure relief valve is opposite to the handedness of said third threads of said main valve.

6. A cryosurgical instrument according to claim 1 wherein said cap has a hole with sixth threads therein complementary to the third threads of said main valve portion, whereby said main valve portion is screwed directly into said cap.

\* \* \* \* \*